(12) United States Patent
Stecco et al.

(10) Patent No.: US 11,833,024 B2
(45) Date of Patent: Dec. 5, 2023

(54) SYSTEMS, DEVICES, AND METHODS FOR RETRIEVAL SYSTEMS HAVING A TETHER

(71) Applicant: AVANTEC VASCULAR CORPORATION, Sunnyvale, CA (US)

(72) Inventors: Kathryn Stecco, Sunnyvale, CA (US); Nicholas DeBeer, Sunnyvale, CA (US); Karl Halden, Sunnyvale, CA (US); Teresa Ruvalcaba, Sunnyvale, CA (US); Frank Becking, La Canada Flintridge, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 554 days.

(21) Appl. No.: 17/101,349

(22) Filed: Nov. 23, 2020

(65) Prior Publication Data
US 2021/0113322 A1    Apr. 22, 2021

Related U.S. Application Data

(63) Continuation of application No. 15/847,473, filed on Dec. 19, 2017, now Pat. No. 10,874,499.
(Continued)

(51) Int. Cl.
*A61F 2/01* (2006.01)
*A61B 17/50* (2006.01)
(Continued)

(52) U.S. Cl.
CPC .............. *A61F 2/011* (2020.05); *A61B 17/50* (2013.01); *A61F 2/01* (2013.01);
(Continued)

(58) Field of Classification Search
CPC ........ A61F 2/01; A61F 2/95; A61F 2002/011; A61F 2002/013; A61F 2002/016; A61F 2002/9528; A61F 2002/9534; A61B 17/221; A61B 17/50; A61B 2017/00287; A61B 2017/00623; A61B 2017/2212; A61B 2017/2215; A61B 2017/2217; A61B 2017/22035
See application file for complete search history.

(56) References Cited

U.S. PATENT DOCUMENTS 3,952,737 A    4/1976  Kimmell, Jr.
4,085,743 A    4/1978  Yoon
(Continued)

FOREIGN PATENT DOCUMENTS

EP    1172073 A1    1/2002
JP    H 10-509623 A    9/1998
(Continued)

OTHER PUBLICATIONS

CN, 201580067678.4 First Office Action, dated Aug. 28, 2018.
(Continued)

*Primary Examiner* — Darwin P Erezo
*Assistant Examiner* — Christian D Knauss
(74) *Attorney, Agent, or Firm* — ONE LLP

(57) ABSTRACT

The embodiments described relate to retrieving temporary Inferior Vena Cava (IVC) filters and other endovascular implants or foreign bodies. Features are provided for effective actuation in closing an inner aperture of the embodiments.

12 Claims, 6 Drawing Sheets

Related U.S. Application Data

(60) Provisional application No. 62/438,277, filed on Dec. 22, 2016.

(51) Int. Cl.
*A61B 17/00* (2006.01)
*A61B 17/22* (2006.01)

(52) U.S. Cl.
CPC ........... *A61B 2017/00367* (2013.01); *A61B 2017/00623* (2013.01); *A61B 2017/22035* (2013.01); *A61F 2002/016* (2013.01); *A61F 2230/005* (2013.01); *A61F 2230/0067* (2013.01)

(56) References Cited

U.S. PATENT DOCUMENTS

| | | | |
|---|---|---|---|
| 4,174,715 A | 11/1979 | Hasson | |
| 4,467,802 A | 8/1984 | Maslanka | |
| 4,611,594 A | 9/1986 | Grayhack et al. | |
| 4,655,219 A | 4/1987 | Petruzzi | |
| 4,723,936 A | 2/1988 | Buchbinder et al. | |
| 4,873,978 A | 10/1989 | Ginsburg | |
| 4,960,411 A | 10/1990 | Buchbinder | |
| 5,011,488 A | 4/1991 | Ginsburg | |
| 5,041,093 A | 8/1991 | Chu | |
| 5,074,845 A | 12/1991 | Miraki et al. | |
| 5,098,440 A | 3/1992 | Hillstead | |
| 5,102,415 A | 4/1992 | Guenther et al. | |
| 5,370,647 A | 12/1994 | Graber et al. | |
| 5,549,626 A | 8/1996 | Miller et al. | |
| 5,601,595 A | 2/1997 | Smith | |
| 5,653,684 A | 8/1997 | Laptewicz et al. | |
| 5,662,671 A | 9/1997 | Barbut et al. | |
| 5,746,251 A | 5/1998 | Bullard | |
| 5,782,747 A | 7/1998 | Zimmon | |
| 5,800,457 A | 9/1998 | Gelbfish | |
| 5,814,064 A | 9/1998 | Daniel et al. | |
| 5,827,324 A | 10/1998 | Cassell et al. | |
| 5,846,251 A | 12/1998 | Hart | |
| 5,908,435 A | 6/1999 | Samuels | |
| 5,911,734 A | 6/1999 | Tsugita et al. | |
| 5,944,728 A | 8/1999 | Bates | |
| 6,001,118 A | 12/1999 | Daniel et al. | |
| 6,152,946 A | 11/2000 | Broome et al. | |
| 6,156,055 A | 12/2000 | Ravenscroft | |
| 6,159,230 A | 12/2000 | Samuels | |
| 6,203,561 B1 | 2/2001 | Ramee et al. | |
| 6,210,370 B1 | 4/2001 | Chi-Sing et al. | |
| 6,238,412 B1 | 5/2001 | Dubrul et al. | |
| 6,241,738 B1 | 6/2001 | Dereume | |
| 6,251,092 B1 | 6/2001 | Qin et al. | |
| 6,251,122 B1 | 6/2001 | Tsukernik | |
| 6,264,671 B1 | 7/2001 | Stack et al. | |
| 6,273,900 B1 | 8/2001 | Nott et al. | |
| 6,290,710 B1 | 9/2001 | Cryer et al. | |
| 6,306,163 B1 | 10/2001 | Fitz | |
| 6,336,934 B1 | 1/2002 | Gilson et al. | |
| 6,395,017 B1 | 5/2002 | Dwyer et al. | |
| 6,443,972 B1 | 9/2002 | Bosma et al. | |
| 6,447,531 B1 | 9/2002 | Amplatz | |
| 6,458,151 B1 | 10/2002 | Saltiel | |
| 6,485,501 B1 | 11/2002 | Green | |
| 6,500,182 B2 | 12/2002 | Foster | |
| 6,569,181 B1 * | 5/2003 | Burns | A61F 2/95 606/198 |
| 6,569,184 B2 | 5/2003 | Huter | |
| 6,602,271 B2 | 8/2003 | Adams et al. | |
| 6,605,102 B1 | 8/2003 | Mazzocchi et al. | |
| 6,632,236 B2 | 10/2003 | Hogendijk | |
| 6,645,222 B1 | 11/2003 | Parodi et al. | |
| 6,663,650 B2 * | 12/2003 | Sepetka | A61F 2/013 606/200 |
| 6,663,652 B2 | 12/2003 | Daniel et al. | |
| 6,679,893 B1 | 1/2004 | Tran | |
| 6,695,813 B1 | 2/2004 | Boyle et al. | |
| 6,699,260 B2 | 3/2004 | Dubrul et al. | |
| 6,702,834 B1 | 3/2004 | Bpylan et al. | |
| 6,743,247 B1 | 6/2004 | Levinson et al. | |
| 6,780,196 B2 | 8/2004 | Chin et al. | |
| 6,800,080 B1 | 10/2004 | Bates | |
| 6,833,002 B2 | 12/2004 | Stack et al. | |
| 6,896,690 B1 | 5/2005 | Lambrecht et al. | |
| 6,958,074 B2 | 10/2005 | Russell | |
| 7,211,089 B2 | 5/2007 | Kear et al. | |
| 7,322,989 B2 | 1/2008 | Teague et al. | |
| 7,338,512 B2 | 3/2008 | McGuckin, Jr. et al. | |
| 7,377,925 B2 | 5/2008 | Poll | |
| 7,491,210 B2 | 2/2009 | Dubrul et al. | |
| 7,625,390 B2 | 12/2009 | Hendriksen et al. | |
| 7,658,747 B2 | 2/2010 | Forde et al. | |
| 7,731,723 B2 | 6/2010 | Kear et al. | |
| 7,780,693 B2 | 8/2010 | Brady et al. | |
| 7,780,694 B2 | 8/2010 | Palmer et al. | |
| 7,837,702 B2 | 11/2010 | Bates | |
| 7,993,362 B2 | 8/2011 | Lowe et al. | |
| 8,038,704 B2 | 10/2011 | Sherburne | |
| 8,043,322 B2 | 10/2011 | Hendriksen et al. | |
| 8,163,004 B2 | 4/2012 | Amplatz et al. | |
| 8,202,309 B2 | 6/2012 | Styrc | |
| 8,273,073 B2 | 9/2012 | Levine et al. | |
| 8,298,244 B2 | 10/2012 | Garcia et al. | |
| 8,469,969 B2 | 6/2013 | Kear et al. | |
| 8,469,970 B2 | 6/2013 | Diamant | |
| 8,475,488 B2 | 7/2013 | Cartier et al. | |
| 8,512,401 B2 | 8/2013 | Murray, III et al. | |
| 8,747,597 B2 | 6/2014 | Rosqueta et al. | |
| 8,795,305 B2 | 8/2014 | Martin et al. | |
| 9,232,956 B2 | 1/2016 | Bonneau et al. | |
| 9,949,816 B2 | 4/2018 | Becking et al. | |
| 2001/0044595 A1 | 11/2001 | Reydel et al. | |
| 2002/0010476 A1 | 1/2002 | Mulholland et al. | |
| 2002/0062135 A1 | 5/2002 | Mazzocchi et al. | |
| 2002/0068967 A1 | 6/2002 | Drasler et al. | |
| 2002/0169474 A1 | 11/2002 | Kusleika et al. | |
| 2002/0193827 A1 | 12/2002 | McGuckin, Jr. et al. | |
| 2003/0130680 A1 | 7/2003 | Russell | |
| 2003/0176884 A1 | 9/2003 | Berrada et al. | |
| 2003/0187474 A1 | 10/2003 | Keegan et al. | |
| 2004/0049226 A1 | 3/2004 | Keegan et al. | |
| 2004/0073230 A1 | 4/2004 | Mulholland et al. | |
| 2004/0093012 A1 | 5/2004 | Cully et al. | |
| 2004/0138677 A1 | 7/2004 | Little et al. | |
| 2004/0153118 A1 | 8/2004 | Clubb et al. | |
| 2004/0181237 A1 | 9/2004 | Forde et al. | |
| 2004/0199202 A1 | 10/2004 | Dubrul et al. | |
| 2005/0049576 A1 | 3/2005 | Snell et al. | |
| 2005/0159770 A1 | 7/2005 | Divani et al. | |
| 2005/0182439 A1 | 8/2005 | Lowe | |
| 2005/0187570 A1 | 8/2005 | Nguyen et al. | |
| 2005/0234502 A1 | 10/2005 | Gilson et al. | |
| 2005/0251197 A1 | 11/2005 | Hensley et al. | |
| 2005/0267515 A1 | 12/2005 | Oliva et al. | |
| 2005/0283166 A1 | 12/2005 | Greenhalgh | |
| 2006/0020256 A1 | 1/2006 | Bell et al. | |
| 2006/0074410 A1 | 4/2006 | Malecki et al. | |
| 2006/0074446 A1 | 4/2006 | Gilson et al. | |
| 2006/0184193 A1 | 8/2006 | Lowe et al. | |
| 2006/0247572 A1 | 11/2006 | McCartney | |
| 2006/0259119 A1 | 11/2006 | Rucker | |
| 2007/0005101 A1 | 1/2007 | Fahey et al. | |
| 2007/0027520 A1 | 2/2007 | Sherburne | |
| 2007/0112374 A1 | 5/2007 | Paul et al. | |
| 2007/0129753 A1 | 6/2007 | Quinn et al. | |
| 2007/0149996 A1 | 6/2007 | Coughlin | |
| 2007/0162048 A1 | 7/2007 | Quinn et al. | |
| 2007/0173884 A1 | 7/2007 | Gilson et al. | |
| 2007/0186933 A1 | 8/2007 | Domingo et al. | |
| 2007/0239254 A1 | 10/2007 | Chia et al. | |
| 2007/0244504 A1 | 10/2007 | Keegan et al. | |
| 2007/0282369 A1 | 12/2007 | Gilson et al. | |
| 2008/0091223 A1 | 4/2008 | Pokorney et al. | |
| 2008/0269774 A1 | 10/2008 | Garcia et al. | |

(56) References Cited

U.S. PATENT DOCUMENTS

| | | |
|---|---|---|
| 2009/0182370 A1 | 7/2009 | Volobuyev et al. |
| 2009/0192485 A1 | 7/2009 | Heuser |
| 2009/0198315 A1 | 8/2009 | Boudjemline |
| 2009/0222035 A1 | 9/2009 | Schneiderman |
| 2009/0222076 A1 | 9/2009 | Figulla et al. |
| 2009/0248060 A1 | 10/2009 | Schneider et al. |
| 2009/0287291 A1 | 11/2009 | Becking et al. |
| 2009/0299393 A1 | 12/2009 | Martin et al. |
| 2010/0030254 A1 | 2/2010 | Chanduszko et al. |
| 2010/0057184 A1 | 3/2010 | Randolph et al. |
| 2010/0137846 A1 | 6/2010 | Desai et al. |
| 2010/0256669 A1 | 10/2010 | Harris et al. |
| 2010/0312268 A1 | 12/2010 | Belson |
| 2010/0331949 A1 | 12/2010 | Habib |
| 2011/0040321 A1 | 2/2011 | Cartier |
| 2011/0046611 A1 | 2/2011 | Christiansen |
| 2011/0125180 A1 | 5/2011 | Tripp et al. |
| 2011/0178547 A1 | 7/2011 | Paul, Jr. et al. |
| 2011/0282274 A1 | 11/2011 | Fulton, III |
| 2011/0288572 A1 | 11/2011 | Martin |
| 2011/0307002 A1 | 12/2011 | Gilson et al. |
| 2012/0010699 A1 | 1/2012 | Vesely |
| 2012/0029607 A1 | 2/2012 | McHugo et al. |
| 2012/0041473 A1 | 2/2012 | Nigon |
| 2012/0089216 A1 | 4/2012 | Rapaport et al. |
| 2012/0123515 A1 | 5/2012 | Hosford et al. |
| 2012/0316638 A1 | 12/2012 | Grad et al. |
| 2013/0053882 A1 | 2/2013 | Hocking et al. |
| 2013/0131690 A1 | 5/2013 | Nagl et al. |
| 2013/0184738 A1 | 7/2013 | Laroya et al. |
| 2013/0197567 A1 | 8/2013 | Brady et al. |
| 2013/0253573 A1 | 9/2013 | Agnew |
| 2013/0267848 A1 | 10/2013 | Fearmot et al. |
| 2013/0289694 A1 | 10/2013 | Sherburne |
| 2013/0297010 A1 | 11/2013 | Bishop et al. |
| 2013/0317589 A1 | 11/2013 | Martin et al. |
| 2014/0005712 A1 | 1/2014 | Martin |
| 2014/0024887 A1 | 1/2014 | Ishii et al. |
| 2014/0155930 A1 | 6/2014 | Bennett et al. |
| 2014/0172008 A1 | 6/2014 | McKinnis et al. |
| 2014/0243878 A1 | 8/2014 | Urbanski et al. |
| 2014/0257362 A1* | 9/2014 | Eidenschink ............. A61F 2/01 606/200 |
| 2014/0277089 A1 | 9/2014 | Goode et al. |
| 2014/0309656 A1 | 10/2014 | Gal et al. |
| 2014/0373334 A1 | 12/2014 | Gamarra et al. |
| 2015/0105819 A1 | 4/2015 | Becking et al. |
| 2015/0133918 A1 | 5/2015 | Sachar |
| 2015/0351775 A1 | 12/2015 | Fulton, III |
| 2015/0366650 A1 | 12/2015 | Zi et al. |
| 2016/0081704 A1 | 3/2016 | Jeon et al. |
| 2016/0095689 A1 | 4/2016 | Becking et al. |
| 2016/0095690 A1 | 4/2016 | Becking et al. |
| 2016/0166370 A1 | 6/2016 | DeBeer et al. |
| 2016/0296315 A1 | 10/2016 | Yachia et al. |

FOREIGN PATENT DOCUMENTS

| | | |
|---|---|---|
| JP | 2003-501203 A | 1/2003 |
| JP | 2004-524049 A | 8/2004 |
| JP | 2005-523767 A | 8/2005 |
| JP | 2007-508902 A | 4/2007 |
| JP | 2008-513121 A | 5/2008 |
| JP | 2008-514276 A | 5/2008 |
| JP | 4109422 B2 | 7/2008 |
| JP | 2009-517124 A | 4/2009 |
| JP | 4320142 B2 | 8/2009 |
| JP | 2013-154183 A | 8/2013 |
| KR | 101133157 B1 | 4/2012 |
| WO | WO 00/16846 A1 | 3/2000 |
| WO | WO 2007/110864 A2 | 10/2007 |
| WO | WO 2017/099786 A1 | 6/2017 |

OTHER PUBLICATIONS

CN, 201480084040.7 Second Office Action, dated Jun. 3, 2019.
EP, 14810754.3 Extended Search Report, dated Nov. 24, 2016.
EP, 14907807.3 Supplementary Search Report, dated May 15, 2018.
EP, 15867928.2 Supplementary Search Report, dated Jun. 5, 2018.
EP, 15867562.9 Supplementary Search Report, dated Jun. 5, 2018.
EP, 16873911.8 Supplementary Search Report, dated May 2, 2019.
EP, 15910402.5 Supplementary Search Report, dated May 13, 2019.
EP, 15910402.5 Extended Search Report, dated Aug. 27, 2019.
EP, 17884666.3 Extended Search Report, Jul. 15, 2020.
EP, 19208256.8 Extended Search Report, dated May 18, 2020.
JP, 2016-519686 Office Action, dated Mar. 28, 2018.
JP, 2017-530592 Office Action, dated Sep. 27, 2018.
JP, 2017-530585 Office Action, dated Jul. 16, 2019.
JP, 2018-529531 Office Action, Sep. 19, 2019.
WO, PCT/US2014/042343 ISR and Written Opinion, dated Sep. 30, 2014.
WO, PCT/US2015/058898 Isr and Written Opinion, dated Feb. 11, 2016.
WO, PCT/US2015/065074 ISR and Written Opinion, dated Mar. 22, 2016.
WO, PCT/US2015/065025 ISR and Written Opinion, dated Apr. 1, 2016.
WO, PCT/US2015/065102 ISR and Written Opinion, dated Sep. 8, 2016.
WO, PCT/US2017/067343 ISR and Written Opinion, dated Mar. 22, 2018.

* cited by examiner

SYSTEMS, DEVICES, AND METHODS FOR RETRIEVAL SYSTEMS HAVING A TETHER

CROSS-REFERENCE TO RELATED APPLICATIONS

This application is a continuation of U.S. patent application Ser. No. 15/847,473, filed Dec. 19, 2017, which claims priority to and the benefit of U.S. Provisional Patent Application Ser. No. 62/438,277, filed Dec. 22, 2016, both of which are incorporated by reference herein in their entireties for all purposes.

FIELD

The embodiments described herein relate to retrieval devices, some embodiments relate to system and methods for endovascular temporary Inferior Vena Cava (IVC) filters.

BACKGROUND

Temporary IVC filters are placed like permanent filters, but are designed so that they may be retrieved in a separate endovascular procedure, generally from a femoral vein or internal jugular vein approach. Most of the currently-available temporary filters include a hook-like feature with which they can be captured and received within a catheter or sheath for removal by employing a gooseneck snare or a multi-loop snare.

While retrieval is a simple procedure in principle, difficulty is often encountered capturing a filter's hook with the snare loop(s). Such difficulty is compounded when the filter is tilted or off-kilter in placement. Several filters are designed to avoid such orientation.

However, the problem remains common because the device is not anchored into the IVC in a stable fashion. Constant blood flow in addition to blood clots can disorient the filter within the IVC making recapture difficult. Accordingly, there exists a need for a filter retrieval system with improved ease of use and/or less susceptibility to problems of filter orientation.

SUMMARY

Example embodiments of systems, devices, and methods for an elongate retrieval device having a tether are provided. In many embodiments, the elongate retrieval device includes a braid structure at the distal end of an elongate shaft, the proximal end of which is accessible to the user directly or by way of a proximal user interface (e.g., a control handle). The braid structure can include one or more layers of braid, and in many embodiments, is configured as a funnel having an interior flap, such that the funnel has a distal opening that is relatively larger than a proximal opening at the proximal edge of the flap.

In many embodiments, one or more tethers can be located at or near the proximal opening. The one or more tethers can have various configurations. In some embodiments, a portion of a tether passes through the braid at the proximal opening and extends across the proximal opening (e.g., like a diameter or chord of a circle or ellipse) in a configuration crossing the proximal opening. In some embodiments, portions of one or more tethers can be arranged to cross both the proximal opening and each other in a symmetrical crossing configuration (e.g., at right angles like a cross-hair in the case of two tether portions) or a non-symmetrical crossing configuration (e.g., where two tether portions cross at non-perpendicular angles). The tether portions of the crossing configuration can also extend at least partially around the peripheral rim of the proximal opening. In some embodiments, a portion of a tether can extend at least partially around the proximal opening, with or without one or more tether portions in a crossing configuration. Additional embodiments are disclosed, including additional embodiments of systems utilizing retrieval devices, and methods of using such systems and/or devices to retrieve a foreign body from within a patient.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1A:
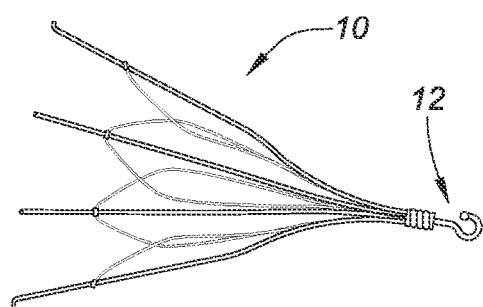
FIGS. 1A and 1B depicts examples of IVC filters usable with the systems and/or methods hereof.

Various exemplary embodiments are described below. Reference is made to these examples in a non-limiting sense, as it should be noted that they are provided to illustrate more broadly applicable aspects of the devices, systems and methods. Various changes may be made to these embodiments and equivalents may be substituted without departing from the true spirit and scope of the various embodiments. In addition, many modifications may be made to adapt a particular situation, material, composition of matter, process, process act(s) or step(s) to the objective(s), spirit or scope of the present invention. All such modifications are intended to be within the scope of the claims made herein.

Before the present subject matter is described in detail, it is to be understood that this disclosure is not limited to the particular example embodiments described, as such may, of course, vary. It is also to be understood that the terminology used herein is for the purpose of describing particular embodiments only, and is not intended to be limiting, since the scope of the present disclosure will be limited only by the appended claims.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

Example embodiments of IVC filter/object retrieval system with improved usability and with less susceptibility to the object's (e.g., IVC filter) orientation issues are disclosed. In some embodiments, the IVC object retrieval system may be used with a wide variety of filter architectures—existing or otherwise. Accordingly, new filters may be designed for use with the disclosed IVC object retrieval system in which fewer design constraints and/or compromises may be required of the filter design. By way of example only, and not to limit the devices with which the embodiments of retrieval systems described herein may be used, examples of filters with which the present embodiments can be used for retrieval or other purposes include existing and/or modified versions of the filters described in any of U.S. Pat. Nos. 3,952,747; 5,601,595; 6,443,972; 7,338,512 and 7,625,390 (all of which are incorporated herein by reference in their entireties for all purposes), with commercially released devices including the OPTEASE, GUNTHER, TULIP, CELECT, DENALI and OPTION, or with others.

Many embodiments of the IVC object retrieval systems include a funnel-shaped apparatus at their distal end. The funnel trap may be constructed of heatset braid, e.g., superelastic (SE) nickel-titanium alloy (nitinol) braid. In some embodiments, the funnel-shaped end of a retrieval device may include a distal rim defining a distal opening, and a more proximal aperture or opening defined at a proximal end of an inner portion (e.g., a flap). When an enlarged proximal end of an IVC filter or other foreign body to be captured is guided past the distal rim of the funnel and through the proximal aperture, the proximal aperture can then be closed (e.g., by cinching) to effect capture of the filter or other foreign body.

In some embodiments, the retrieval system includes loop-type features that are actuatable to close the proximal aperture. As described in commonly-owned PCT Application No. PCT/US15/65102 (United States Publication No. 2016/0095689) a strand of material may be used to extend as a tether to the proximal end of the retrieval system for actuation. Example of spliced-loop lasso and tether systems are described therein.

In some embodiments, the retrieval system includes an aperture actuation apparatus having a non-spliced or two-ended loop, which provides better or more effective aperture actuation. The non-spliced or two-ended loop lasso provides a more complete aperture or opening closure, with less required user input (in terms of length to pull and/or force to actuate) to close aperture.

In some embodiments, the non-spliced (or two-ended) loop is formed by a length of tether (e.g., a suture, cord, fiber or filament, formed from, e.g., polymeric, metallic (e.g., nitinol) or a hybrid or composite materials, or others) with two free ends. To add stability to the loop structure, one or both ends of the tether may pass or cross through opposite-side strand material adjacent the loop opening. This can ultimately yield a two-ended tether setup for the loop. The non-spliced loop can offer the added benefit of tether members acting in parallel (e.g., as in a parallel spring arrangement) to limit stretch associated with forceful system manipulation.

In some embodiments, the retrieval system may include a crossing structure of tether material or other filament(s) at the proximal aperture. In certain embodiments, the crossing structure is a separate feature are not integrated with the encircling lasso. Separating the crossing structure (e.g., cross-hairs) from the loop allows for their independent actuation and associated improvement in proximal aperture closure.

With separate loop and cross-hair features, the tethers can, in some embodiments, be arranged as four solo strands. In some embodiments, the tether of the retrieval system may include two sets (e.g., two strands with two ends). In other embodiments, a tripod configuration may be formed using a set of two tethers (those for the loop) and two others (those for the cross-hairs). These embodiments offer a measure of symmetry in applying tension (or resisting tension) around the aperture as compared to single-tether approaches. In some embodiments, the retrieval system may employ two, three and four legged symmetry options. Stated otherwise, 2-way, 3-way and 4-way symmetry tethering systems may be employed. Or still further, options are provided with bilateral, trilateral and/or quadrilateral symmetry.

In the embodiments with the two sets of strands, these sets of strands may be synergistically employed in connection with a pair of additional support struts. A first pair of tether strands may be received within a first tubular support strut and a second pair of tether strands may be received in a second tubular support strut, the struts may be sized so that tether pull that would otherwise draw the inner flap and proximal aperture inward (or more proximally) is supported to avoid such action. By maintaining proximal aperture position with the system, bowing of the overall funnel construct that can otherwise occur is limited.

Various construction embodiments for the support struts are presented below. Likewise, the support struts may be used in configurations other than the paired option. A single support strut may be employed.

Another optional set of features concern the manner of tether attachment and/or configuration within the system. The incorporated Int'l Publ. No. PCT/US15/65102 (United States Publication No. 2016/0095689) shows and describes tethers glued or potted at a proximal end of the device. In some embodiments, the tether(s) may be connected to a core member that extends from the proximal end to at least mid-way or more preferably to within at least about 2 to 10 cm of the distal end of the device. Such a core member is configured (e.g., by material selection and/or physical geometry) to be stiffer or offer less elasticity than the otherwise full-length tether material. In some embodiments, the tether strands may be attached to a polyethylethylketone (PEEK) rod. Using a polymer rod or tube allows it to be easily cut-through, which can provide a "bail out" feature by removing tether tension to open the aperture for releasing an embedded foreign object (such as a "stuck" IVC filter). In some embodiments, a metal wire core member (e.g., stainless steel, CoCr or nitinol) could likewise be used.

In some embodiments, applying tension on the tethers may cause the proximal opening (or aperture) to close and releasing the tension may cause the proximal opening to re-open from the closed position.

In some embodiments, the retrieval system includes a tensioning and de-tensioning mechanism that includes multiple tethers. The multiple tethers could be twisted around or relative to each other to shorten their effective length and tighten the lasso and/or cross-hairs associated with the proximal aperture. The multiple tethers tensioning and de-tensioning mechanism is highly controllable in that each full turn adds a fine gradation of axial tension and/or movement. Moreover, the same twisting approach to tighten the tethers and aperture in a foreign-object retrieval procedure can be applied in manufacture for pre-loading and/or removing unwanted slack from the lasso and/or cross-hairs.

The multiple tethers tensioning and de-tensioning mechanism also serves as an actuation mechanism (or user interface) that is both accurate and with tactile-feedback without complex machining, gearing or other user interface requirements. The actuation mechanism may be actuated by applying torque or to twist-up the tethers (directly or via an intermediate shaft such as described above).

In some embodiments, a user interface is threaded and works in conjunction with the twist-up of the suture strand (s). By applying treads or threading to interfacing members, a hybrid actuation system is created. It is hybrid in the sense that the combination of tether twist and tread advancement (or retraction) controls aperture actuation. Such a system may easily incorporate a hemostatic and/or a detent or clicker feature for audibly and/or tactically counting actuation turns.

The subject delivery and/or retrieval devices, kits in which they are included (with and without assembly), methods of use and manufacture (including assembly of the constituent components in vivo or ex vivo) are all included within the scope of the present disclosure. Some aspects of the same are described above, and more detailed discussion is presented in connection with the figures below.

Figure 1B:
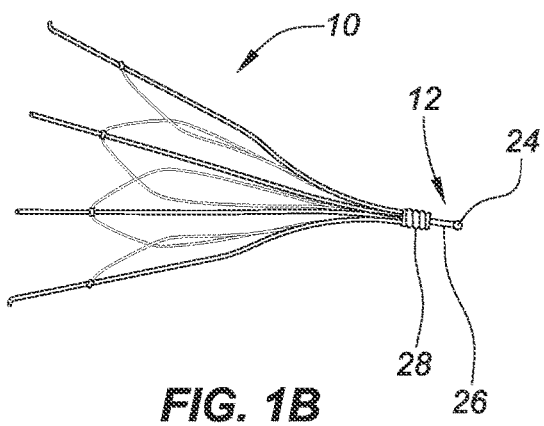

FIG. 1A shows a GUNTHER TULIP (Cook Medical, Inc.) temporary IVC filter 10 with a retrieval interface 12 configured with a hook end. FIG. 1B shows an IVC filter 10 where, instead of a hook, the retrieval interface 12 of IVC filter 10 has a nubbin-type interface 22. The nubbin (itself) may comprise a laser-formed or solder-formed protuberance or bump 24 on an extension 26 from a hub 28. Alternatively, as shown in FIG. 2, filter retrieval interface 12 may comprise a band 24' (e.g., a Pt marker band) mounted (e.g., by swaging, welding, gluing, etc.) on extension 26.

Figure 2:
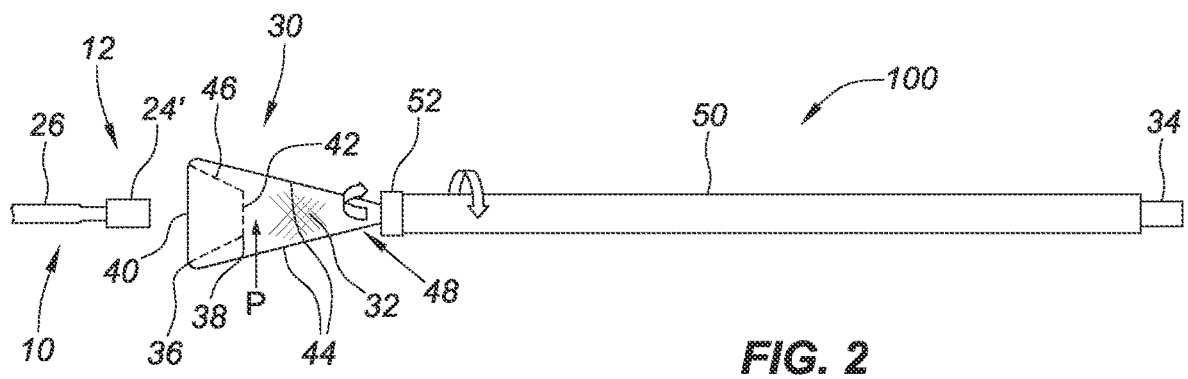
FIG. 2 is a side view depicting an example embodiment of a retrieval system.

FIG. 2 provides an overview of a retrieval system 100 in which the features further described may be incorporated, in accordance with various embodiments of the disclosure. Retrieval system 100 includes a funnel-trap structure 30, which may be made of a heatset braid material 32. In some embodiments, funnel-trap structure 30 may be a flexible distal extension to an elongate shaft 34, which can (in some embodiments) be slidably positioned within an elongate sleeve 50. In some embodiments, elongate sleeve 50, which may be a commercially available catheter or sheath or a custom part of retrieval system 100 configured for advancement through the patient's vasculature, may include a distal radiopaque marker band 52. In some embodiments, elongate sleeve 50 can be omitted or otherwise configured to remain outside of the patient's body.

In some embodiments, braid 32 may comprise nitinol (e.g., such as that which is superelastic (SE) at human body temperature), CoCr, Stainless Steel or another biocompatible material. Braid 32 may comprise of material having between 72 and 288, or between about 144 and 192 filament "ends" in a 1-over-1, 1-over-2, 2-over-2 or other pattern. In some embodiment, the SE nitinol wire may be between about 0.001 and about 0.002 inches in diameter. At this diameter range, a mesh of SE nitinol wire provides a supple and relatively "smooth" matrix surface from which to construct the flexible funnel-trap. The value of such a surface is in its atraumatic aspect and/or ability to help guide an IVC filter interface or other foreign body to be captured into position for capture even if it is oriented off-angle. Still, other wire sizes and/or end counts in a braid or other construction options are possible as well.

To assist with target device or foreign body capture or recapture, funnel trap structure 30 may be selectively directable. As indicated by the arrows in FIG. 2, the material from which structure 30 is made can be heatset or otherwise configured to provide a bias in an angular direction. The angle of deployment of structure 30 may be selectable or fully straightened by relative position of a core member or obturator (not shown) or by a sleeve or catheter sheath. Further positioning may be achieved by rotating the device as further illustrated. Alternatively, sleeve 50 may be shaped to flex shaft 34 to set trap structure 30 position.

Figure 3:
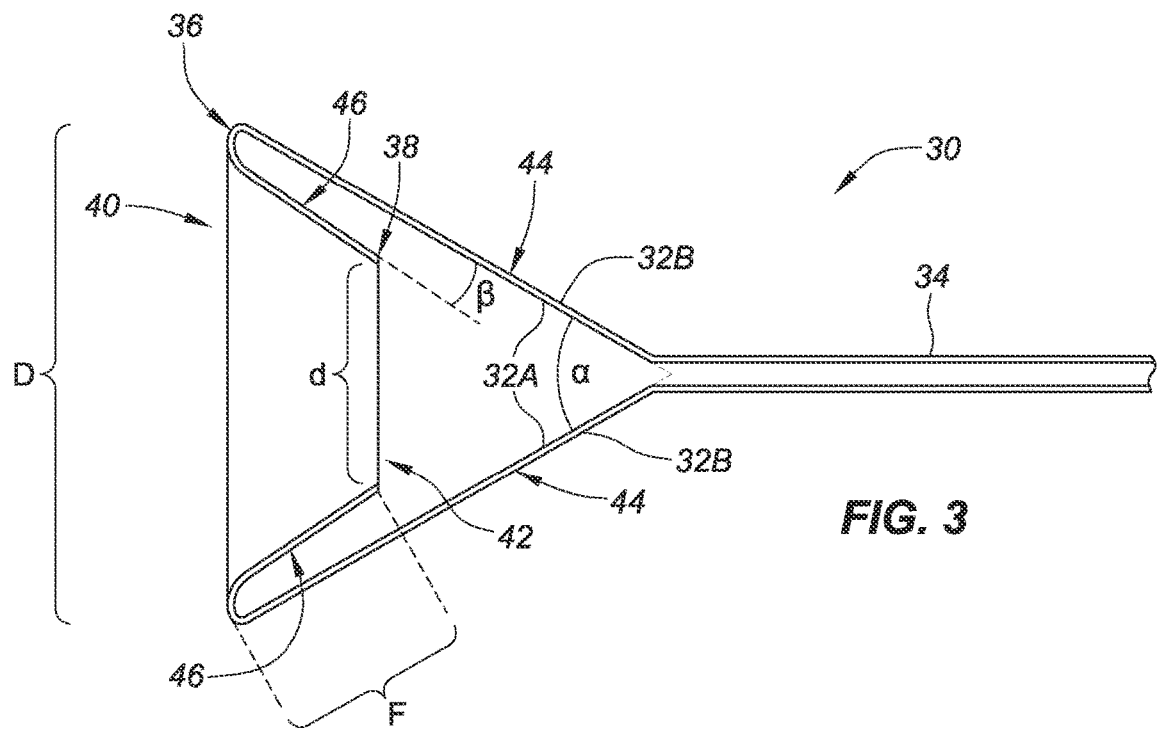
FIG. 3 is a side-sectional view depicting another example embodiment of a retrieval system.

Trap structure 30 may be generally frusto-conical in shape as shown or otherwise configured. With an outer conical shape (e.g., a triangular shape in cross section as shown in FIG. 3) structure 30 is highly supportive, yet provides a flexible "waist" section 48 for the directable feature options noted above. Still, the device may be bowed outward along its sides or otherwise configured.

In some embodiments, a distal rim opening (or aperture) 40 of structure 30 may be larger than its proximal rim opening 42 to create a structure that tapers down in the distal to proximal direction. In this way, filter engagement feature 24' (as shown in FIG. 2) of device 10 (e.g., an IVC filter) may be guided along braid material 32 and through proximal opening 42. Once the end of device 10 has passed through opening 42, and optionally bottomed-out at or near section 48, it can be releasably captured and retained by reducing the width of openings 40 and/or 42 (e.g., at least partially closing or constricting openings 40 and/or 42). Such action is further described below. In some embodiments, a pocket (P) may be formed within the substantially conical or frusto-conical braid wall 44.

In some embodiments, upon capturing device 10, structure 30 can be withdrawn from the patient's body without first retracting structure 30 into an outer sleeve (e.g., device 50) and then withdrawing from the body through an introducer sheath located at the percutaneous opening. In other embodiments, after capturing device 10, structure 30 can be withdrawn into sleeve 50 and then device 10, structure 30, and sleeve 50 can be withdrawn together through an introducer sheath and out of the patient's body. The retrieval process may be visualized fluoroscopically by a physician during the medical procedure.

In some embodiments, the catheter or pusher shaft 34, sleeve 50 or other catheters or sheaths used in or with the system may comprise of medical grade plastics such as PTFE, FEP, PEEK, PI, etc. Alternatively, they may be constructed using conventional catheter construction techniques and include a liner, braid support and outer jacket (not shown), metal hypotube, etc. In embodiments intended for tracking through a guide or delivery catheter without an incorporated sheath, a loading sheath may be employed. Any such loading sheath may be pre-split or splittable. Other typical percutaneous access instruments (such as wires, etc.), valves and other hardware may also be employed in accordance with various embodiments, including medical treatment methods.

Trap structure 30 can be made as a subassembly and attached to its catheter or pusher shaft 34. U.S. Publ. No. 2016/0095690 and U.S. Publ. No. 2015/0105819, both of which are incorporated by reference in their entireties for all purposes, describe example embodiments of steps in the manufacture of a braid portion 30 of device 100.

Structure 30 can include one or more layers of braid 32. FIG. 3 is a cross-sectional view depicting an example embodiment of structure 30 having an inner layer 32A and an outer layer 32B of braid. In some embodiments, layers 32A and 32B are formed by fastening or securing two discrete layers of braid together (e.g., by adhesive, by one or more connectors, etc.). In the embodiment depicted here, braid 32 is one continuous sheet or tube of braid that is folded back over itself to form the two layers 32A and 32B. The position where braid 32 is folded back upon itself to form the two layers is indicated by reference numeral 38, and can be referred to as a first fold in braid 32. The two layers 32A and 32B of braid 32 can also be folded at a second location, indicated by reference numeral 36, which can be referred to as a second fold in braid 32. Configuration in this manner results in an inner funnel or flap 46 within an outer funnel formed by braid wall 44.

In the embodiment of FIG. 3, the peripheral rim of distal opening 40 is formed by second fold 36 and the peripheral rim of proximal opening 42 is formed by first fold 38. Inner layer 32A and outer layer 32B of braid 32 can be set in the shape depicted in FIG. 3 by heat-setting using conventional techniques (e.g., in a furnace, salt pot, etc.). In many embodiments, distal opening 40 is larger than proximal opening 42, although other configurations are possible.

In some embodiments, for IVC filter retrieval, braid portion of structure 30 may have a diameter (D) from about 5 mm to about 20 mm, or more preferably about 10 to about 15 mm (e.g., size in a range to work within average size human IVCs where such vessels are reported as having a mean diameter of 20 mm within a range of 13 to 30 mm). The braid portion may have a length (L) ranging from about 10 mm to about 30 mm). Structure 30 may have an overall cone angle ($\alpha$) (between braid walls 44) ranging between 30 to 90 degrees. In some embodiments, an angle ($\beta$) of bend 36 between braid wall 44 and flap 46 may be between about 0 and about 60 degrees, and flap length (F) may be between about 1 and about 10 mm in length.

Distal opening 40 may have a diameter (d) between about 1.5 and 4 mm. In some embodiments, the diameter of distal opening 40 may be between 2.5-3 mm (for retrieving commercially-available IVC filter devices). Distal opening 40 of structure 30 may be set perpendicularly relative to a device axis. Otherwise, it may be angled or have a more complex shape.

Figure 4:
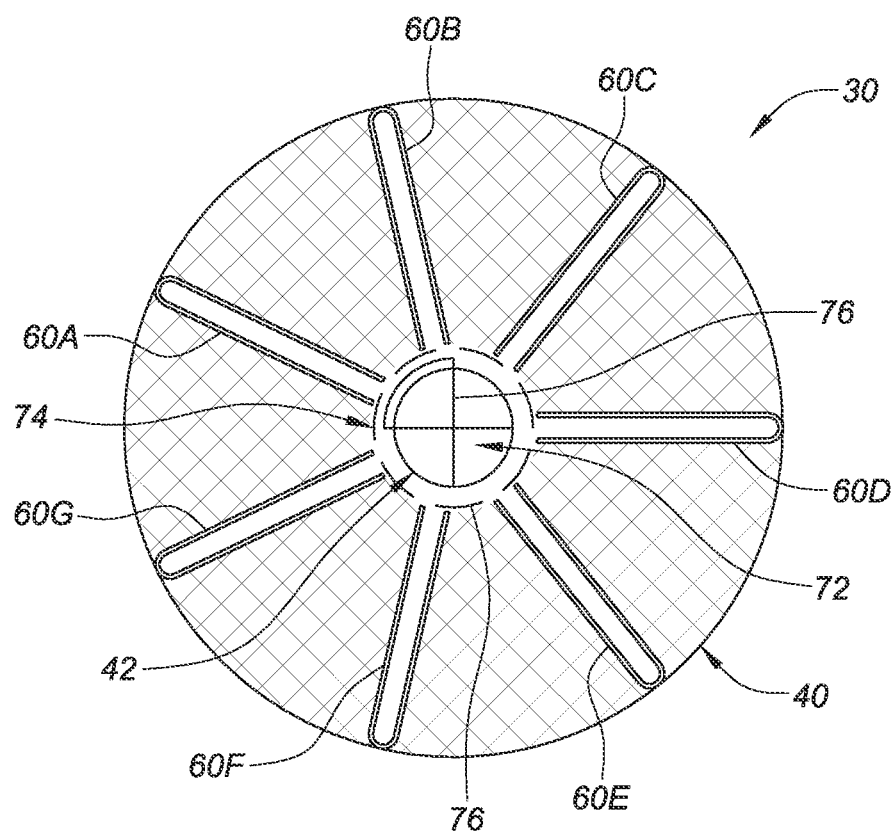
FIG. 4 is an end-view depicting an example embodiment of the braided portion of a retrieval device.
Figure 5:
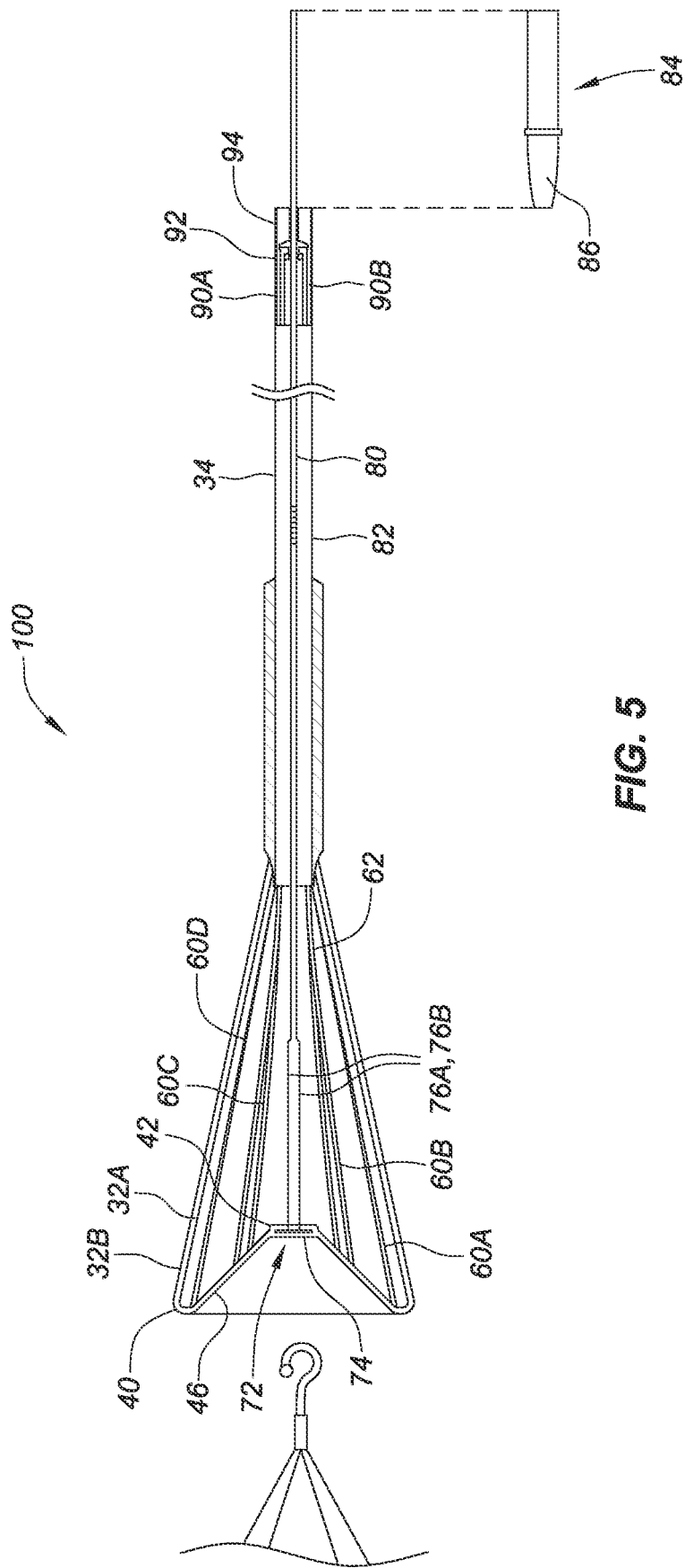
FIG. 5 is a partial side-sectional view depicting an example embodiment of a retrieval system.

FIG. 4 is an end-on view of an example embodiment of structure 30. In this embodiment, structure 30 includes a support member having elongate members 60A, 60B, 60C, 60D, 60E, 60F, and 60G. Any number of one or more elongate members 60 can be used. In embodiments where structure 30 includes multiple braid layers 32A and 32B, the support member(s) can be interposed between braid layers 32A and 32B. Support members 60 can additionally, or alternatively, be located on the inner-most side of inner braid layer 32A as shown in FIG. 5, which is a partial cross-sectional view depicting another example embodiment of device 100. Further optional details of support member construction and/or placement are presented in Int'l Publ. No. WO 2016/094676, which is incorporated by reference herein in its entirety for all purposes.

FIG. 4 also shows a crossing arrangement 74 of a tether 76 formed from suture material (e.g., ultra-high-molecular-weight polyethylene (UHMWPE) suture) extending across the inner proximal aperture 42 of the braid in accordance with some embodiments of the disclosure. In some embodiments, the strands are symmetrical, resembling a crossing configuration 72. Any symmetrical or non-symmetrical crossing configuration can be used. Here, one section of a tether 76 is arranged to twice bisect proximal opening 42 at right angles. In some embodiments, only a single tether section can extend across proximal opening 42, e.g., such in the form of a diameter or chord of a circle, where no second tether section nor crossing pattern is implemented. In other embodiments, a first discrete tether section (having two ends) can extend across proximal opening 42 and a second discrete tether section (having two different ends) can extend across proximal opening 42 such that the two discrete tether sections form the crossing configuration 72.

Another section of tether 76 can be used to form a loop configuration 74 that at least partially encircles (here the loop fully encircles) proximal opening 42. Loop configuration 74 is shown positioned outside of crossing configuration 72 for ease of illustration, where in practice loop configuration 74 will be in contact with or in close proximity to innermost braid at proximal opening 42. In one embodiment, a single section of tether (having two ends) is woven through proximal opening 42 to form both the crossing configuration 72 and loop configuration 74.

In the embodiment of FIG. 5, the position of (at least some) of tethers 76 can be seen between braid layers 32A and 32B at or adjacent to proximal opening 42 (e.g., at or near the internal radius thereof). In some embodiments, one or more tethers 76 form cross-hair 72 and/or loop 74 configurations at the distal opening 40 and/or proximal opening 42 and then the one or more tethers 76 extend proximally towards and/or into shaft 34. Tethers 76 can be used to constrict or allow expansion of openings 40 and/or 42. Here, two tethers 76A and 76B are shown coupled with proximal opening 42, although others may be included as will be described in more detail herein.

Tethers 76A and 76B can hold the inner flap 46 from pulling out or everting, for example, in the event of forceful device withdrawal where the medical device to be captured is one that includes a hook interface 12. Tethers 76A and 76B can also provide a mechanism for actuating closure of opening or aperture 42.

As shown in FIG. 5, tethers 76A and 76B are connected to a core member 80 (which may be tube, wire or rod) positioned within shaft 34. The tethers may be glued in a slot, across flats and/or located within an overlying sheath or cover 82 receiving adhesive to effect connection.

Tethers 76A and 76B can be pulled or tensioned using core member 80 to tighten down the associated loop 74 and/or cross-hair 72 features. In some embodiments, core member 80 is omitted and tethers 76A and 76B extend to the proximal end of the device to user interface such as a slide or gear-type device handle. However, core member 80 is useful in that is can be configured to provide greater stiffness (less elasticity) than full-length suture tether(s). In some embodiments, cross-hair configuration 72 is present at proximal opening 42, while loop configuration 74 is present at distal opening 40. In still further embodiments, loop configurations 74 are present at both distal opening 40 and proximal opening 42, while a cross-hair configuration is present at proximal opening 42. In still further embodiments, both distal opening 40 and proximal opening 42 have both cross-hair 72 and loop 74 configurations.

Also, core member 80 can provide a stable user-interface platform as well as surface area against which to form a seal. With core member 80 extending from the proximal end of shaft 34, it offers a position to affix a standard torquer 84.

With a torquer tightened down and connected to core member 34, twisting the parts together while stabilizing shaft 34 transfers rotation to tethers 76. The twisting (like twisting up a common playground swing) results in tether shortening or tensioning that is applied to the loop and/or cross-hairs.

The number of rotations applied using the torquer can be counted by including a visual guide or cue on the torquer (such as blacked-out region 86 optionally formed by laser etching or engraving). A seal complex (comprising a pair of sleeves 90A, 90B affixed to core member to define an O-ring groove, an O-ring 92 in that groove and a stop 94 that is press-fit or glued into sleeve 34) is advantageously provided as well.

System 100 in FIG. 5 shows two tethers 76A and 76B. However, it should be understood that the perspective shown might be illustrative of two grouped pairs of tethers or four tethers—with only half of them showing due to the sectional nature of the view. As detailed further below, other tether configurations are possible as well.

Figure 6:
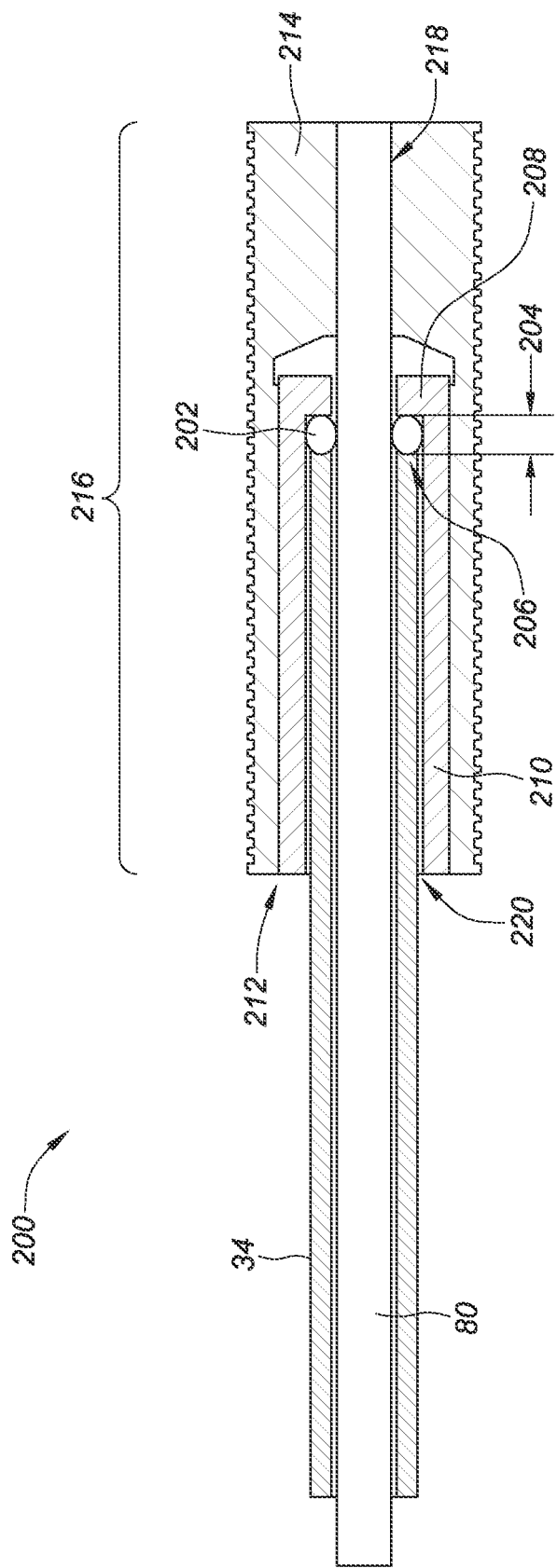
FIG. 6 is a side-sectional view depicting an example embodiment of a user interface for a retrieval device.

FIG. 6 depicts an example embodiment of a user interface 200 that can be manually held by the user outside of the patient's body. As in system 100, a concentric arrangement of a core member 80 and a shaft sleeve 34 are shown. Core member 80 may extend outside shaft 34. Also, provision is made for an O-ring 202 (shown compressed) in a groove 204. However, O-ring 202 may be relatively larger than in the FIG. 5 assembly. This is possible without compromising system profile as groove 204 in this configuration is between a proximal end or face 206 and a wall 208 of a sleeve 210.

Sleeve 210 may include threading 212 that mates or matches with that of an outer torquer body 214, which may include a knurled or checkered pattern 216 for user grip.

Torquer body 214 may be connected to core member 80 with adhesive 218 or by other means. Threaded sleeve 210 may be connected to shaft 34 by adhesive 220 or other means. When turning torquer body 214 and gripping shaft 34 (which may also be textured for improved grip, such as by media blasting), torquer body 214 either advances distally or retracts proximally with the direction of the threading. To count or otherwise track the number or revolutions or turns applied, the components can be tactically and/or audibly counted by incorporating a detent or click feature(s) in the gap (G) between sleeve 210 and torquer body 214.

In some embodiments, torquer body 214 may be turned (e.g., clockwise employing left-handed threads) so that it pulls back (e.g., moves proximally) while the tethers are also being twisted, which results in the closing or constricting of opening 42. As such, significantly fewer turns with system 200 are needed to tighten the aperture loop 74 and/or cross-hairs 72 as compared to other closing methods where the torquer is setup only to rotate.

Depending on the thread pitch selected (e.g., 4-40 standard or M1 threads), highly accurate adjustment can be made. Essentially, by "counting turns or partial turns" a physician can actually observe and precisely control device actuation under fluoroscopy during a medical procedure. The same holds true for the system in FIG. 4, but it requires additional actuation turns for the desired level of aperture closure for certain IVC filter capture. The sub-system in FIG. 4 can be configured for equivalent tether tensioning and aperture closure with about half, a third or even a quarter as many turns.

In both embodiments (e.g., system 100 in FIG. 5 and system or sub-system 200 in FIG. 6), internal friction (e.g., as provided in predictable fashion by the O-ring or such other seal architecture as may be employed) between various components of the system prevents "back-drive" or inadvertent untwisting once tension is applied. However, intentionally reversing or "taking turns off" of the torquer body 84 or 214 will cause it to untwist the tethers. This allows loosening at opening or aperture 42 and release of a captured implant, if desired. With the threading included between sleeve 210 and torquer body 214, the core member is also advanced—with such combined action (e.g., with translation) causing such a result with fewer turns (e.g., as with tightening above).

Accordingly, system 200 may be regarded as a type of hybrid user interface. It is hybrid in the sense that it uses threads/threading for axial or translative action in conjunction with the twist-up tightening option also described.

Figure 7C:
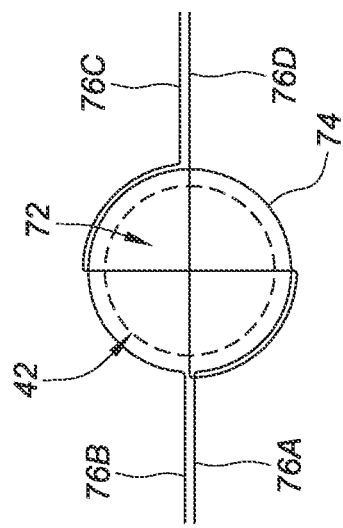
FIGS. 7A-7C depict example embodiments of strand patterns.
Figure 7B:
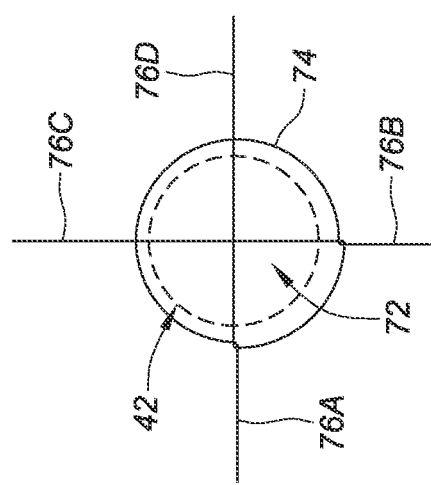
Figure 7A:
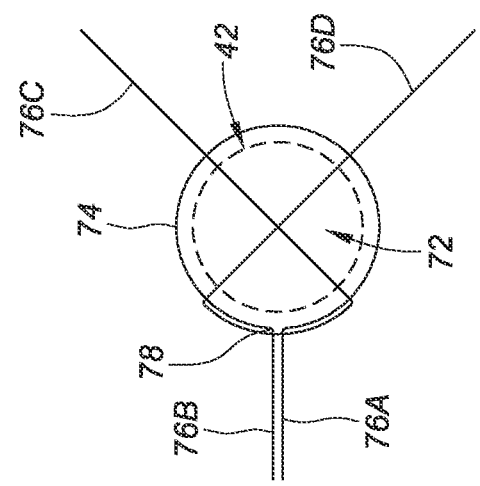

Turning now to FIGS. 7A-7C, these figures illustrate different loop 74 and cross-hair (or X-shaped) 72 sewing or threading patterns for location at or adjacent to proximal opening 42. The configuration of loop 74 can extend entirely around proximal opening 42 (FIG. 7A), substantially entirely around proximal opening 42 (FIG. 7C), or partially around proximal opening 42 (FIG. 7B). Typically, loop 74 will be fit or located between braid layers 32A and 32B at first fold 38. The tethers that form the cross-hair configuration (or any other crossing pattern) may be located above or below loop 74 at or adjacent to proximal opening 42.

As shown in FIGS. 7A-7C, the exit directions of each tether strands around proximal opening 42 may be at the same location at different locations. In some embodiments, one or more of the tether strands cross over and bend around the adjacent braid toward the proximal end (user interface end). In some embodiments, as shown in FIG. 7A, one of the strands may pass through another at a crossing point 78 in the loop configuration. Alternatively, this pass-through feature may be omitted and each strand is simply adjacent to each other.

Referring to FIG. 7B, the material defining cross-hairs 72 is partially incorporated in defining loop 74 in the lower-left quadrant. The meeting points of strands (e.g., 76A/76D and 76B/76C) may involve pierced crossing points or a twisted, woven or intertwining approach as shown. Proximally directed force (e.g., pull) on each of the four tethers effects independent tightening of each length interacting with opening/aperture 42.

Figure 8A:
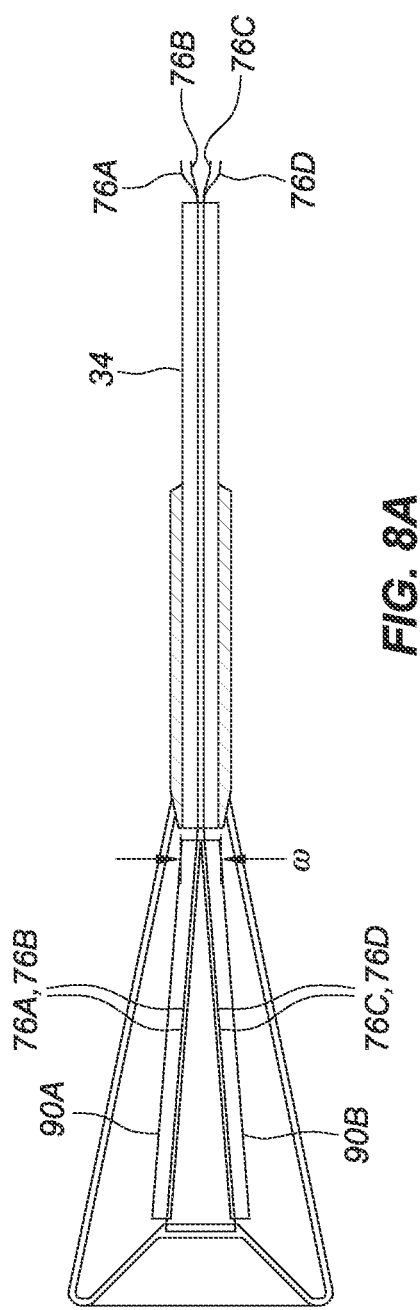
FIGS. 8A and 8B are partial side-sectional views depicting example embodiments of retrieval devices with different proximal aperture or rim support-strut configurations.

With the approach in FIG. 7C, two pairs of tethers (76A/76B and 76C/76D) may exit loop 74 at opposite sides. This configuration offers several advantages. In some embodiments (as shown FIG. 8A), each paired set of tethers can be received within a support sleeve or strut 90A, 90B. Configured as shown, the struts "float" as they are held in place by the concentric arrangement of the tether sections.

In some embodiments, each strut is abutted proximally at the distal end of shaft 34 and distally at the rim of proximal opening 42. When the tethers are pulled, the rim remains stable in position, with the struts in compression and tether tension transmitted to the loop and/or cross-hairs to at least partially close opening 42.

To improve strut fit, the struts may be ovalized or flattened along their length. Such a configuration allows for side-by-side suture reception and/or minimal combined width (W) where the pieces come together (e.g., proximally within the trap section 30 when deployed, but along their entire length when collapsed in sheath 50).

Other construction options are possible as well. For example, the struts may be formed by extending and bisecting sleeve 34 and covering those portions with thin walled (e.g., 0.003-0.005 inch) tubing. In such an arrangement, the sleeves will contain the tethers and the shaft extensions will be bear compressive load(s).

Without the struts, support members 60A, 60B, etc. may be included in the construct such as shown in FIGS. 4 and 5. Or both support member(s) 60 and the strut(s) 90 may be employed (although not shown) in combination.

Figure 8B:
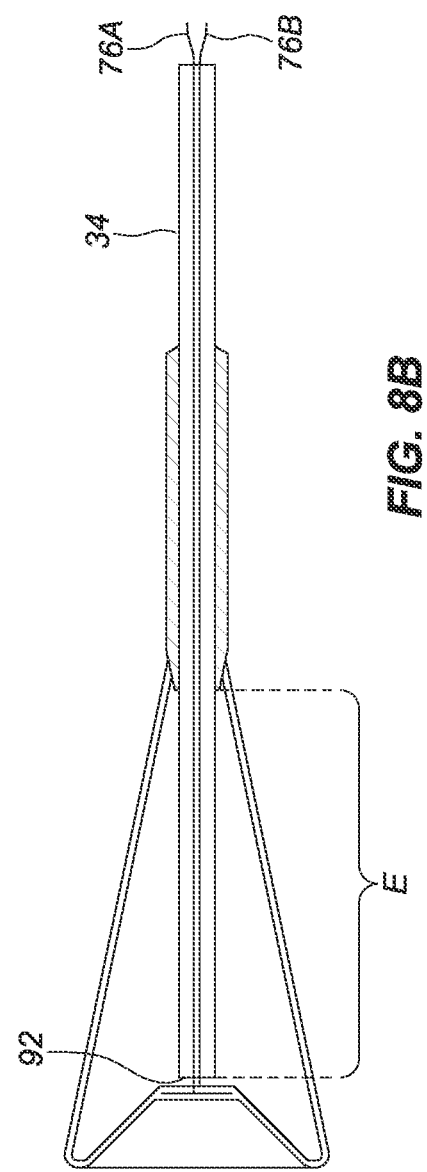

FIG. 8B illustrates another support strut configuration in accordance with some embodiments. In this case, as single support column is provided as an intact extension of shaft 34. The extension (E) may be curved, canted or bent, or incorporate a switch-back or S-turn so that its end 92 does not align with the center of opening 42. However, this is an option as are other (associated) possible cross-hairs and/or loop configurations. As shown, only two tethers 76A and 76B are provided in this example. They may synch a two-ended loop, alone, to close opening 42 or be otherwise used.

The embodiments described herein are restated and expanded upon in the following paragraphs without explicit reference to the figures. In many example embodiments, an endovascular medical device is provided that includes an elongate shaft connected to a flexible distal extension including a braid, the braid having a distal rim defining a distal opening and a proximal rim defining a proximal opening, where the shaft and the flexible distal extension are configured for insertion into vasculature of a patient; a portion of a tether extending through the braid at the proximal rim across the proximal opening; and a proximal user interface configured to tension the tether.

In some embodiments, the braid has a first fold that forms two layers of the braid, and the two layers have a second fold, where the second fold is at the distal rim of a funnel-shaped structure and the first fold is at the proximal rim of the funnel-shaped structure. In some embodiments, the portion of the tether extends across the proximal opening twice in a crossing configuration.

In some embodiments, the portion of the tether is a portion of a first tether, and the medical device further includes a portion of a second tether arranged as a loop at least partially encircling the proximal rim. The portion of the second tether can be arranged as a loop between the two layers of braid. In some embodiments, the portion of the second tether fully encircles the proximal opening.

In some embodiments, the first tether has two ends, and the second tether has two ends, the two ends of the first tether being received within a first tubular strut, and the two ends of the second tether being received within a second tubular strut. The first and second tubular struts can be positioned between the proximal opening of the flexible distal extension and a distal end of the elongate shaft.

In some embodiments, the medical device further includes a core member received within the shaft, wherein the tether is connected at a distal end of the core member. The proximal user interface can include a torquer connected or affixed to the core member. The medical device can further include an externally threaded interface, where the torquer is internally threaded. In some embodiments, the medical device further includes a sleeve connected at a proximal end of the elongate shaft, the sleeve including the externally threaded interface.

In some embodiments, the first tether and second tether extend proximally from the proximal opening toward the proximal user interface. In some embodiments, the second tether crosses the proximal opening twice to form a right angle crossing configuration.

In some embodiments, the proximal opening is configured to capture a retrieval interface of an inferior vena cava (IVC) filter.

In many embodiments, a medical method for retrieving a foreign body is provided, the medical method including: advancing an endovascular medical device in a patient's vasculature, the medical device comprising: an elongate shaft connected to a flexible distal extension comprising a braid, the braid having a distal rim defining a distal opening and a proximal rim defining a proximal opening; a portion of a tether extending through the braid at the proximal rim across the proximal opening; passing a portion of the foreign body to be retrieved through the proximal opening; and tensioning the tether with the foreign body extending through the proximal opening.

In some embodiments, the method further includes twisting opposite ends of the tether around each other to achieve the tensioning. In some embodiments, the method further includes supporting the proximal opening with at least one strut during the tensioning.

In some embodiments, the method further includes withdrawing the foreign body from the patient's vasculature with the endovascular medical device.

In some embodiments, the tether is a first tether in a crossing configuration, the endovascular medical device further comprising a second tether in a loop configuration around the proximal rim. In some embodiments, the method further includes tensioning the first tether and the second tether with the foreign body extending through the proximal opening.

In some embodiments, the foreign body is an inferior vena cava (IVC) filter and the portion of the foreign body is a retrieval interface of the IVC filter.

The subject methods, including methods of use and/or manufacture, may be carried out in any order of the events which is logically possible, as well as any recited order of events. Embodiment methods may include any of a hospital staffs activities associated with device provision, implant positioning, re-positioning, implant or device retrieval and/or release.

Furthermore, where a range of values is provided, it is understood that every intervening value, between the upper and lower limit of that range and any other stated or intervening value in the stated range is encompassed within the invention. Also, it is contemplated that any optional feature of the inventive variations described may be set forth and claimed independently, or in combination with any one or more of the features described herein.

Though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention.

Reference to a singular item includes the possibility of a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity. Accordingly, the breadth of the different inventive embodiments or aspects described herein is not to be limited to the examples provided and/or the subject specification, but rather only by the scope of the issued claim language.

The invention claimed is:

1. An endovascular medical device comprising:
a funnel-shaped braid structure having a distal portion folded back inwardly to form a distal opening and a proximal opening;
an elongate shaft coupled to the funnel-shaped braid structure; and
a first tether coupled to a portion of a rim of the proximal opening and to a proximal user interface, the first tether extending across the proximal opening in a crossing configuration, wherein the first tether is configured to constrict the proximal opening when the proximal user interface is actuated.

2. The endovascular medical device of claim 1, wherein the first tether is disposed between layers of braid.

3. The endovascular medical device of claim 1, further comprising a core member received within the elongate shaft, wherein the tether is connected at a distal end of the core member.

4. The endovascular medical device of claim 3, wherein the proximal user interface comprises a torquer connected to the core member.

5. The endovascular medical device of claim 4, wherein the torquer comprises internal threads.

6. The endovascular medical device of claim 5, further comprising a sleeve connected at a proximal end of the elongate shaft, the sleeve comprises an externally threaded interface.

7. An endovascular medical device comprising:
a funnel-shaped braid structure having a distal portion folded back inwardly to form a distal opening and a proximal opening;
an elongate shaft coupled to the funnel-shaped braid structure;
a first tether coupled to a portion of a rim of the proximal opening and to a proximal user interface, wherein the first tether is configured to constrict the proximal opening when the proximal user interface is actuated; and
a second tether at least partially encircling the rim of the proximal opening, the second tether crosses the proximal opening twice to form a right-angle crossing configuration.

8. The endovascular medical device of claim 7, wherein the second tether fully encircles the proximal opening.

9. The endovascular medical device of claim 7, wherein the second tether is disposed between layers of braid.

10. The endovascular medical device of claim 7, wherein the first tether and second tether extend proximally from the proximal opening toward the proximal user interface.

11. The endovascular medical device of claim 7, further comprising a first and second tubular strut, wherein the first tether comprises two ends being threaded through the first tubular strut, and the second tether comprises two ends being threaded through the second tubular strut.

12. The endovascular medical device of claim 7, further comprising first and second tubular struts positioned between the proximal opening and a distal end of the elongate shaft.

* * * * *